United States Patent [19]
Reis

[11] Patent Number: 5,846,195
[45] Date of Patent: Dec. 8, 1998

[54] TONGUE DEPRESSOR FOR MEDICAL USE

[75] Inventor: Carlos Cezar Barros Reis, Rio De Janeiro, Brazil

[73] Assignee: Cezar Reis Promocoes Comerciaias Ltda., Rio De Janeiro, Brazil

[21] Appl. No.: 721,115

[22] Filed: Sep. 26, 1996

[30] Foreign Application Priority Data

Mar. 29, 1996 [BR] Brazil .................................. 9601207-2

[51] Int. Cl.⁶ ...................................................... A61B 11/02
[52] U.S. Cl. ............................................................ 600/240
[58] Field of Search ..................................... 600/235, 237, 600/238, 240, 242; 606/234, 235; 426/104, 801, 512, 516, 517

[56] References Cited

U.S. PATENT DOCUMENTS 3,315,664  4/1967  Hill ........................................... 600/240
5,176,151  1/1993  Hardinu ................................ 600/240 X

*Primary Examiner*—Beverly M. Flanagan
*Attorney, Agent, or Firm*—Woodard, Emhardt, Naugton Moriarty & McNett

[57] ABSTRACT

A tongue depressor for medical use comprising a non-toxic thermoplastic material and an aromatic sweetener and/or its derivatives, which are molded by process of injection molding originating an article of vibrant colors, with taste and smell, being 8 to 20 cm long, 1 to 4 cm wide and 0.1 to 0.3 cm thick.

4 Claims, 1 Drawing Sheet

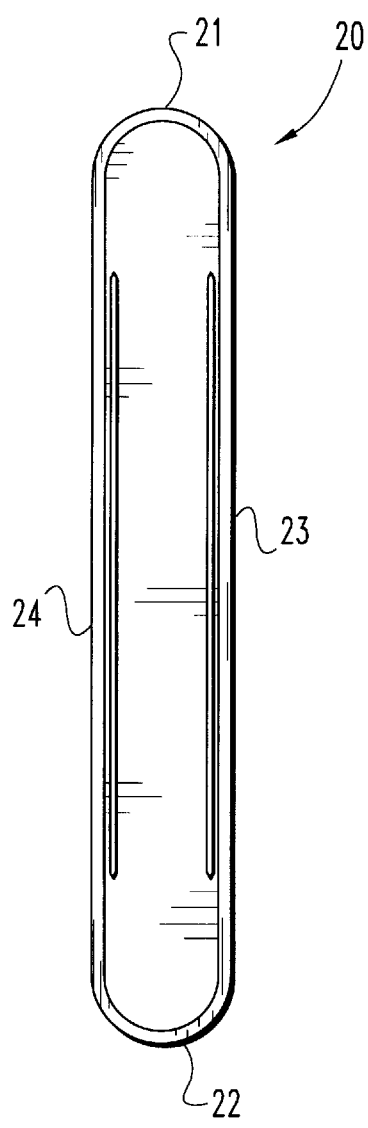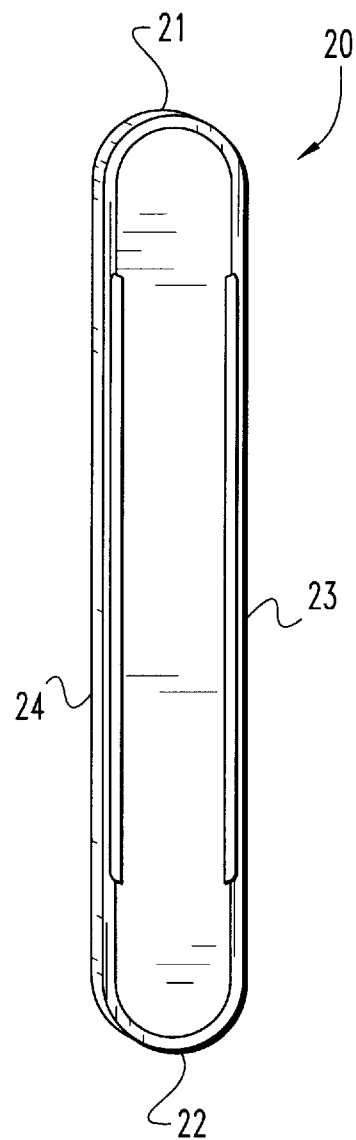
*Fig. 1*  *Fig. 2*

TONGUE DEPRESSOR FOR MEDICAL USE

BACKGROUND OF THE INVENTION

1. Field of the Invention

The present invention relates to spatulas or tongue depressors for medical use, more specifically, to spatulas containing ingredients that create taste and smell as part of the thermoplastic material used for the spatula.

2. Description of the Prior Art

Spatulas for medical use have been widely used in the prior art. However, until the present moment, only those made of wood have been used and this presents some drawbacks. Since they are made of wood, these spatulas may generate splinters, which may hurt the patient's tongue. Another drawback is that, in the event the wooden spatulas are not appropriately stored, that is, in dry places or, at least, with little humidity, there will be a rapid growth of certain fungus on the surfaces of same, resulting in contamination of the patient through infection.

SUMMARY OF THE INVENTION

The present invention is directed to tongue depressors for medical use, with taste and smell ingredients and comprising a non-toxic thermoplastic material, e.g., polypropylene polystyrene of high impact, or similar material. Blended into the material is an aromatic sweetener and/or derivative thereof. The tongue depressor of the present invention is molded by a process of injection molding, generating an article 8 to 20 cm long, 1 to 4 cm wide and 0.1 to 0.3 cm thick. The spatulas or tongue depressors manufactured according to the above description are, additionally, individually wrapped and sealed in transparent plastic bags.

The manufacture of the spatulas from plastic material presents, primarily, the advantages of hygiene, specially with respect to an article for medical use, in which hygiene is of paramount importance. Apart from this detail of the material, the invention comprises one important innovative characteristic, mainly in the pediatrics field. It is known that it is quite difficult to obtain a diagnosis with a child having sore throat, specially because it is necessary to use an article (a spatula) with the objective of depressing his/her tongue, in order to enable a more accurate diagnosis. This procedure, no doubt, causes a certain discomfort to the child, who is already weak and irritated as a consequence of the illness. Thus, the objective of the present invention is to ease this situation for both the child and the doctor who is treating the child, while providing a new spatula capable of stimulating the curiosity of the child while stimulating her/his sense of sight, smell and taste.

With the objective of making the spatula visually attractive to the child, it is proposed that same be made in vibrant colours, for example, pink, lime, lemon, bright yellow and so forth.

The present invention comprises a further step in the prior art by introducing in the market an article in perfect harmony with the technological development which the current medical practice requires.

BRIEF DESCRIPTION OF THE DRAWINGS

FIG. 1 is a top plan view of a tongue depressor according to the present invention.

FIG. 2 is a perspective view of the FIG. 1 tongue depressor.

DESCRIPTION OF THE PREFERRED EMBODIMENT

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring to FIGS. 1 and 2 there is illustrated a tongue depressor 20 according to the present invention. Tongue depressor 20 is preferably between 8 and 20 cm. in length between rounded ends 21 and 22. The width of tongue depressor 20 is preferably between 1 and 4 cm. from side 23 to side 24. Tongue depressor 20 is a relatively thin member having a thickness of between 0.1 and 0.3 cm.

Tongue depressor 20 is made from a non-toxic thermoplastic material by means of an injection molding process. In order to create a pleasing smell or odor as well as a pleasing taste, an aromatic sweetener is blended into the thermoplastic material and is thus molded into tongue depressor 20. The addition of the aromatic sweetener enables a tongue depressor to be created which will be pleasing to infants and small children.

It is also envisioned that color pigment can be added in order to mold tongue depressor 20 in a vibrant color which would stimulate the curiosity and sense of sight of the child. Colors such as pink, lime, lemon and bright yellow are suggested. When the tongue depressor 20 is used, the aromatic sweetener will stimulate the smell and taste senses of the child.

The tongue depressor 20 is less likely to be affected by the growth of fungus or other bacteria on the surface. Additionally, tongue depressor 20 according to the present invention is able to be individually wrapped in a plastic bag or other wrapping to keep the tongue depressor protected.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A tongue depressor for medical use comprising:

a molded member fabricated from a non-toxic thermoplastic material in combination with an aromatic sweetener are molded by a process of injection molding, said molded member having a length of between 8 cm. and 20 cm., a width of between 1 cm. and 4 cm., and a thickness of between 0.1 cm. and 0.3 cm.

2. A tongue depressor, according to claim 1, in which the thermoplastic material comprises a polystyrene of high impact.

3. A tongue depressor for medical use comprising:

a molded member fabricated from a non-toxic thermoplastic material in combination with an aromatic sweetener are molded by a process of injection molding, said molded member having a thickness of between 0.1 cm and 0.3 cm.

4. A tongue depressor for medical use comprising:

a molded member fabricated from a non-toxic, high impact polystyrene material in combination with an aromatic sweetener, said high impact polystyrene material including a color pigment in order to produce a tongue depressor with a predetermined color, said molded member being molded by a process of injection molding and having a length dimension of between 8 cm. and 20 cm., a width dimension of between 1 cm. and 4 cm., and a thickness of between 0.1 cm. and 0.3 cm.

* * * * *